(12) United States Patent
Tegg et al.

(10) Patent No.: US 8,684,999 B2
(45) Date of Patent: Apr. 1, 2014

(54) CATHETER SHAFT AND METHOD OF MANUFACTURE

(75) Inventors: Troy T. Tegg, Elk River, MN (US);
Richard E. Stehr, Stillwater, MN (US);
Allan M. Fuentes, Mound, MN (US);
Linda K. Nemec, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1858 days.

(21) Appl. No.: 11/967,784

(22) Filed: Dec. 31, 2007

(65) Prior Publication Data
US 2009/0165881 A1 Jul. 2, 2009

(51) Int. Cl.
*A61M 25/00* (2006.01)
*B29D 22/00* (2006.01)
*B29D 23/00* (2006.01)
*B32B 1/08* (2006.01)

(52) U.S. Cl.
USPC .......... 604/523; 428/36.91; 138/137; 138/141

(58) Field of Classification Search
USPC ........ 428/36.91; 138/137, 141; 604/524, 523, 604/525, 526, 527
See application file for complete search history.

(56) References Cited

U.S. PATENT DOCUMENTS

| | | | |
|---|---|---|---|
| 4,636,346 A * | 1/1987 | Gold et al. ................. | 264/139 |
| 4,776,334 A | 10/1988 | Prionas | |
| 4,817,613 A | 4/1989 | Jaraczewski et al. | |
| 4,863,442 A | 9/1989 | DeMello et al. | |
| 4,934,049 A | 6/1990 | Kiekhafer et al. | |
| 5,215,614 A | 6/1993 | Wijkamp | |
| 5,308,342 A * | 5/1994 | Sepetka et al. ................. | 604/525 |
| 5,368,564 A | 11/1994 | Savage | |
| 5,395,328 A | 3/1995 | Ockuly et al. | |
| 5,782,900 A | 7/1998 | de la Rama et al. | |
| 6,001,095 A | 12/1999 | de la Rama et al. | |
| 6,106,510 A * | 8/2000 | Lunn et al. ................. | 604/525 |
| 6,235,021 B1 | 5/2001 | Sieben | |
| 6,500,285 B2 * | 12/2002 | Pepin et al. ................. | 156/86 |
| 6,783,521 B2 * | 8/2004 | Ponzi et al. ................. | 604/527 |
| 6,946,173 B2 * | 9/2005 | Lim et al. ................. | 428/35.2 |
| 6,979,312 B2 * | 12/2005 | Shimada ................. | 604/95.01 |
| 7,229,437 B2 | 6/2007 | Johnson et al. | |
| 7,234,225 B2 | 6/2007 | Johnson et al. | |

(Continued)

FOREIGN PATENT DOCUMENTS

EP 0303487 2/1989

OTHER PUBLICATIONS

PCT Intenational Search Repor and Wrten Opinion of the Intenatonal Searching Authory for PCT/US08/87511 dated Feb. 17, 2009.

*Primary Examiner* — Justin Jonaitis
(74) *Attorney, Agent, or Firm* — Wiley Rein LLP (57) ABSTRACT

A method of manufacturing a catheter assembly generally includes providing a catheter shaft having an outer layer and an inner reinforcing layer; removing at least a portion of the outer layer from a length of the distal end of the catheter shaft in order to expose a distal segment thereof; providing an inner jacket segment; axially engaging the inner jacket segment with an interior surface of the distal segment of the catheter shaft; providing an outer jacket segment around at least the exposed exterior region of the distal segment of the catheter shaft; and bonding the distal segment of the catheter shaft to the inner jacket segment and the outer jacket segment.

29 Claims, 9 Drawing Sheets

(56) References Cited

U.S. PATENT DOCUMENTS

| | | | |
|---|---|---|---|
| 2003/0225391 A1* | 12/2003 | Cragg et al. | 604/508 |
| 2004/0000046 A1* | 1/2004 | Stinson | 29/426.4 |
| 2004/0143256 A1 | 7/2004 | Bednarek | |
| 2005/0065586 A1 | 3/2005 | Johnson | |
| 2005/0214492 A1* | 9/2005 | Zhong et al. | 428/36.91 |
| 2006/0151923 A1 | 7/2006 | Wilkowske et al. | |
| 2007/0299424 A1* | 12/2007 | Cumming et al. | 604/527 |
| 2008/0091169 A1* | 4/2008 | Heideman et al. | 604/527 |

* cited by examiner

CATHETER SHAFT AND METHOD OF MANUFACTURE

BACKGROUND OF THE INVENTION a. Field of the Invention

The instant invention relates to catheters that are used in the human body. In particular, the instant invention relates to a catheter assembly using multiple polymeric sections incorporating varying materials along its longitudinal axes to improve manufacturability of catheter shafts.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

Since the path through the patient's vasculature to the intended site is often long and tortuous, steering forces typically must be transmitted over relatively great distances. Accordingly, it is desirable for a catheter to have sufficient axial (e.g., column) strength to be pushed through the patient's vasculature via a force applied at its proximal end ("pushability"). It is also desirable for a catheter to transmit a torque applied at the proximal end to the distal end ("torqueability"). Pushability and torqueability (collectively, "maneuverability") permit a physician to manipulate a catheter to an intended site and then properly orient the catheter. It is also desirable for a catheter to have sufficient flexibility to substantially conform to the patient's vasculature and yet resist kinking as it does so. Kinking is often the result of a localized failure of the material of the catheter when localized stresses exceed the yield strength of the material.

Once the working end of a catheter has been maneuvered to the desired location, the characteristics of the treatment site may require that the distal or working area of the catheter have different flexibility, hardness or shape characteristics than the main shaft of the catheter.

To provide pushability, torqueability, flexibility, and kink resistance, many extant catheters are made of engineering polymer materials reinforced with metallic wire reinforcing layers. However, the characteristics of pushability, torqueability, flexibility, and kink resistance which are suitable to the main shaft of a catheter may not be appropriate for the working end of the device. As such, different combinations of engineered polymer materials and reinforcement wires may be required at a catheter tip than across the main body of the catheter.

BRIEF SUMMARY OF THE INVENTION

It is desirable to provide a catheter with improved flexibility, kink resistance, and maneuverability which also allows for the distal working end of the catheter to have different and customized maneuverability and mechanical properties from its main shaft.

It is also desirable to be able to more easily manufacture a catheter having a distal tip with mechanical properties that are different from those of the catheter's main shaft.

The foregoing and other aspects, features, details, utilities, and advantages of the present invention will be apparent from reading the following description and claims, and from reviewing the accompanying drawings.

Disclosed herein is a method of manufacturing a catheter assembly, generally including the following steps: providing a catheter shaft having a proximal end, a distal end, an outer layer, and an inner reinforcing layer; removing at least a portion of the outer layer from a length of the distal end of the catheter shaft (e.g., by grinding or laser removal) in order to expose a distal segment of the catheter shaft having an exposed exterior region; providing an inner jacket segment having a proximal end and a distal end; axially engaging the inner jacket segment with an interior surface of the distal segment of the catheter shaft; providing an outer jacket segment around at least the exposed exterior region of the distal segment of the catheter shaft; and bonding the distal segment of the catheter shaft to the inner jacket segment and the outer jacket segment. It is contemplated that the outer jacket segment and the outer layer may be different materials with different durometer hardness values. In some embodiments of the invention, the length of the exposed distal segment of the catheter shaft is at least as long as the length of the inner jacket segment.

Optionally, the catheter shaft may include an inner layer. At least a portion of the inner layer may be removed from a distal end of the catheter shaft to form an exposed interior region of the distal segment of the catheter shaft, wherein the exposed interior region is disposed around the inner jacket segment.

Typically, the outer layer of the catheter shaft, the inner jacket segment, and the outer jacket segment will include melt processing polymers. Suitable materials include, without limitation, polyamides, polyurethanes, polyesters, functionalized polyolefins, polycarbonates, and any combinations thereof. Other suitable materials include, but are not limited to, polyamide-based thermoelastic elastomers, polyester-based thermoplastic elastomers, thermoplastic polyurethanes, styrenic thermoplastic elastomers, and any combinations thereof. It is also contemplated that the outer jacket segment may have varying hardness along its length (e.g., by incorporating a plurality of longitudinal segments of differing material hardnesses).

Optionally, the inner jacket segment may include a pull ring operatively connected thereto, for example at a proximal end of the inner jacket segment.

The method also may include applying energy to the outer jacket segment, the exposed distal segment of the catheter shaft, and the inner jacket segment to form a substantially unitary catheter shaft. A heat-shrink tube may be formed about the outer jacket segment prior to applying energy. It is desirable for the energy to be applied to the outer jacket segment, the exposed distal segment of the catheter shaft, and the inner jacket segment in a manner that does not heat the proximal end of the catheter shaft. That is, it is desirable to apply energy in a manner that does not heat a portion of the outer layer of the catheter shaft which is disposed away from the distal end of the catheter shaft.

According to another aspect of the invention, a method of forming a catheter assembly includes the following steps: providing a catheter shaft having an outer layer of a first material and an inner reinforcing layer; removing at least a portion of the outer layer from a length of the catheter shaft in order to expose a distal segment of the catheter shaft; providing an inner jacket segment having a proximal end and a distal end; axially engaging the exposed distal segment of the catheter shaft with the proximal end of the inner jacket segment, providing an outer jacket segment of a second material around the exposed distal segment of the catheter shaft; and bonding the catheter shaft to the outer jacket segment and the inner jacket segment.

In some embodiments of the invention, the inner reinforcing layer of the catheter shaft extends continuously over the entire length of the catheter shaft and the inner jacket and outer jacket segments.

Also disclosed herein is a catheter assembly formed according to a method generally including the following steps: providing a catheter shaft having a proximal end, a distal end, an outer layer and an inner reinforcing layer; removing at least a portion of the outer layer from a length of the distal end of the catheter shaft in order to expose a segment of the catheter shaft; providing an inner jacket segment having a proximal end and a distal end; axially engaging the exposed segment at the distal end of the catheter shaft with the inner jacket segment such that the inner jacket segment is positioned within and adjacent the exposed segment of the catheter shaft; and forming an outer jacket segment around the exposed catheter shaft segment to operatively connect the catheter shaft to the inner jacket segment. Of course, the outer jacket segment may have a varying hardness along it length, such as a lower durometer than the catheter shaft (e.g., the outer layer of the catheter shaft). It is also contemplated that the inner jacket segment may include a pull ring attached to an inner layer of the inner jacket segment, and the pull ring may also be operatively connected to a plurality of pull wires that extend through the inner jacket segment and catheter shaft to a proximal end of the catheter shaft.

In yet another embodiment of the present invention, a catheter assembly includes: a catheter shaft having an axial length, a proximal end, a distal end, an outer layer of a first material, and an inner reinforcing layer; an outer jacket segment of a second material having an axial length, a proximal end, and a distal end, the second material being different from the first material; the catheter shaft operatively connected at its distal end to the proximal end of the outer jacket segment; and the inner reinforcing layer of the catheter shaft extending throughout the entire axial length of the catheter shaft and the outer jacket segment. Of course, the axial length of the outer jacket segment may include materials of different durometer hardness. In some embodiments, the axial length of the outer jacket segment has an arcuate shape, which may optionally be either fixed or flexible.

In still another embodiment of the invention, a method of manufacturing a catheter assembly generally includes the following steps: providing a catheter shaft having a proximal end, a distal end, an outer layer of a first material, and an inner reinforcing layer; removing at least a portion of the outer layer from a length of the distal end of the catheter shaft in order to expose a distal segment of the catheter shaft having an exposed exterior region; providing an outer jacket segment of a second material around at least the exposed exterior region of the distal segment of the catheter shaft, the second material being different from the first material; and bonding the outer jacket segment to the exposed exterior region of the distal segment of the catheter shaft.

The step of bonding the outer jacket segment to the exposed exterior region of the distal segment of the catheter shaft may include applying energy to the outer jacket segment and the distal segment of the catheter shaft. It is desirable for the energy to be applied in a manner that does not heat the proximal end of the catheter shaft.

Optionally, the method includes providing an inner jacket segment at an interior surface of the distal segment of the catheter shaft; and bonding the inner jacket segment to the interior surface of the distal segment of the catheter shaft. Bonding the outer jacket segment to the exposed exterior region of the distal segment of the catheter shaft and bonding the inner jacket segment to the interior surface of the distal segment of the catheter shaft may include applying energy to the outer jacket segment, the inner jacket segment, and the distal segment of the catheter shaft.

In still another embodiment, the present invention provides a catheter assembly including: a catheter shaft having an axial length, a proximal end, a distal end, an outer layer of a first material and an inner reinforcing layer, at least a portion of the outer layer having been removed from the distal end of the catheter shaft in order to expose a distal segment of the catheter shaft; and an outer jacket segment of a second material having an axial length, a proximal end, and a distal end, the second material being different from the first material; wherein the catheter shaft is operatively connected at its distal segment to the outer jacket segment such that the outer jacket segment substantially replaces the portion of the outer layer that has been removed from the distal end of the catheter shaft in order to form a substantially unitary catheter shaft; wherein the inner reinforcing layer of the catheter shaft extends throughout the entire axial length of the catheter shaft and the outer jacket segment. Of course, the first material and the second material may have different durometer hardness values. Similarly, the first material may be a melt processable polymer and the second material may be another melt processable polymer.

In some embodiments, the catheter shaft includes an inner layer of a third material, the inner reinforcing layer being sandwiched between the outer layer and the inner layer, and further including an inner jacket segment of a fourth material having an axial length, a proximal end, and a distal end, the inner jacket segment being bonded to the inner layer at the distal segment of the catheter shaft.

In still other embodiments, the catheter shaft includes an inner layer of a third material, the inner reinforcing layer being sandwiched between the outer layer and the inner layer, at least a portion of the inner layer having been removed from the distal end of the catheter shaft at the distal segment of the catheter shaft, and further including: an inner jacket segment of a fourth material having an axial length, a proximal end, and a distal end; wherein the catheter shaft is operatively connected at its distal segment to the inner jacket segment such that the inner jacket segment substantially replaces the portion of the inner layer that has been removed from the distal end of the catheter shaft in order to form a substantially unitary catheter shaft. The third material and the fourth material may have different durometer hardness values.

DETAILED DESCRIPTION OF THE INVENTION

The present invention provides a catheter suitable for use in the human vasculature for known medical procedures, such as cardiac mapping and ablation. Catheters utilizing catheter shafts according to the present invention advantageously exhibit improved maneuverability, flexibility, and kink resistance. For purposes of this description, the invention will be described in connection with an elongate electrophysiology catheter. It is contemplated, however, that the described features and methods may be incorporated into any number of catheters as would be appreciated by one of ordinary skill in the art. Examples of catheters particularly appropriate to the present invention include, but are not limited to, fixed curve catheters, conformable catheters, bi-directional catheters, steerable catheters, introducer catheters, diagnostic catheters, and ablation catheters, both irrigated and non-irrigated.

Many electrophysiology catheters such as those listed above are introduced into the vasculature in a similar manner at convenient points on the body (such as a femoral artery). Once introduced, if the ultimate target of the catheter is an organ such as the heart, the path followed to arrive at the final target tissue may be very similar regardless of what the working end of the catheter is ultimately intended to accomplish. Thus, the mechanical properties of the main shaft of a catheter navigating through the tortuous paths of the vasculature are usually similar regardless of the particular type of device being directed to the site. For instance, the main shaft of the catheter is typically soft and flexible enough to be easily manipulated along its length in a manner that allows it to twist and turn through many branches of the vascular system. At the same time, the main shaft should not be so soft that it becomes susceptible to kinking while it is being pushed at its proximal end. It should also have sufficient hardness to resist kinking when it comes into contact with an obstruction, such as a vessel wall.

To improve maneuverability, flexibility, and kink resistance, many catheters utilize one or more reinforcing layers in their construction. For example, the guiding catheter disclosed in U.S. Pat. No. 4,817,613 to Jaraczewski et al. ("Jaraczewski") includes a pair of braided torque transmitting layers sandwiched between a flexible tubular member and a flexible plastic casing applied as a viscous material and subsequently cured. Jaraczewski also teaches, however, that to a certain degree, flexibility comes at the expense of torqueability. Further, depending on the thickness of the torque transfer layers, they may increase the wall thickness, thereby either increasing the overall diameter of the catheter for a given bore size or decreasing the bore size for a given overall diameter.

In contrast, once a catheter has been maneuvered through the vasculature to its ultimate target, it may be desirable for the distal, working end of the catheter to have different physical and mechanical properties than its main shaft. For instance, it may be desirable to provide a mapping catheter with an extremely soft tip at its working end which allows it to easily conform to a variety of different shapes presented by the tissue. In another situation, it may be desirable to provide the working end of the catheter with a harder, fixed shape, such as a loop, which can conform to the shape of well known parts of the anatomy.

Thus, the mechanical properties required to allow the main shaft of a catheter to navigate to a particular site may be different, even dramatically different, from the mechanical properties desired for the working end or tip of the catheter.

Traditional methods of manufacturing reinforced catheters having variable mechanical properties along their length have utilized a reflow process for the entire shaft, which is time consuming and expensive to manufacture. The present invention describes a catheter having a continuous inner reinforcing layer throughout its length and a working end or tip with different mechanical properties from those of the main shaft. Also described are alternative methods of manufacturing which do not require the entire catheter assembly to be reflowed at the same time.

Referring now to the figures, an electrophysiology catheter assembly will be described. The catheter components will be collectively referred to as a "catheter assembly" as they are assembled. Throughout the figures, reference will be made to a catheter assembly comprising a "catheter shaft" and a "catheter segment" or "tip" which are axially connected to one another. The designation of these components is made for convenience only and is not meant to limit or suggest the number of segments or the relative lengths of the axial segments within the spirit of the invention. For instance, a "catheter shaft" need not necessarily be greater in length than a "catheter segment" or "tip." Similarly, a "catheter segment" or "tip" need not necessarily be the most distal portion of the catheter.

Figure 1:
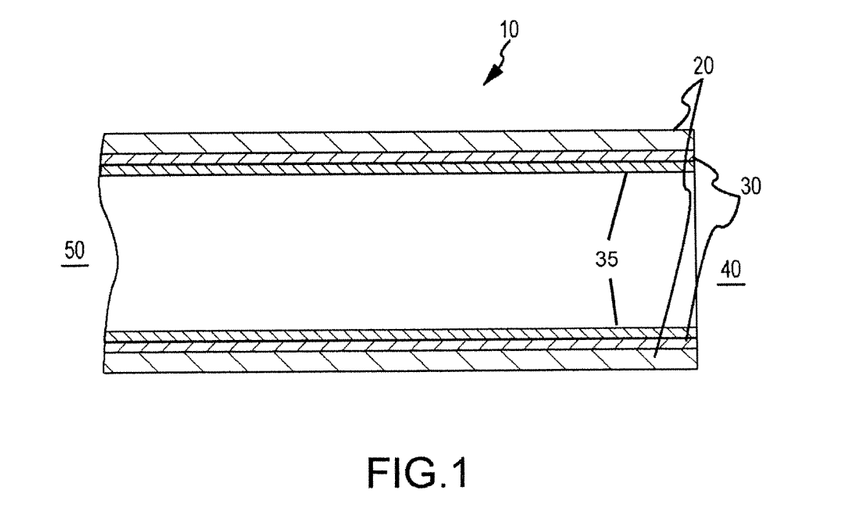
FIG. 1 is a longitudinal cross-sectional view of a reinforced catheter shaft according to an embodiment of the present invention.

With regard to a particular embodiment as shown in FIG. 1, the catheter assembly may include an extruded and reinforced catheter shaft 10 having an outer wall or layer 20, an inner wall or layer 35, a proximal end 40, a distal end 50 and an inner reinforcing layer 30 running through the interior length of the catheter shaft.

Outer wall 20 and inner wall 35 may be a melt-processable polymeric tube, such as extruded polytetrafluoroethylene (PTFE) tubing (e.g., Teflon® brand tubing), optionally including surface etching. Outer wall 20 and inner wall 35 may also be made of other melt processing polymers, including, without limitation, etched polytetrafluoroethylene, polyether block amides, nylon, and other thermoplastic elastomers. One such elastomer is Pebax®, made by Arkema, Inc. Pebax of various durometers may be used, including, without limitation, Pebax 30D to Pebax 70D. In a particular embodiment, inner wall 35 may use Pebax 60D to Pebax 72D. Of course, one of ordinary skill in the art will appreciate how to select suitable materials for the outer wall 20 and inner wall 35 of the catheter shaft depending on the particular application of catheter 10.

Inner reinforcing layer 30 may be a tube of braided metal wire or any other reinforcing material as is known to those of skill in the art. For instance, the inner reinforcing layer may instead be made of non-metallic fibers such as carbon fibers, polymeric fibers, kevlar fibers, or any other material known to those of skill in the art. The fibers in an inner reinforcing layer may also be arranged in a manner other than a "braid." For instance, fibers may be wound on a tube in a helical fashion at any number of angles and pitches. Wound fibers may be combined in layers as well, with different layers of fibers wound in complimentary or contrasting directions. Fibers may be wound or braided in a separate step or may actually be wound into an existing polymeric tube. It should also be appreciated that an inner reinforcing layer need not necessarily form an enclosed "tube." For instance, a helical reinforcing layer wound in a manner that creates spaces between helical revolutions is within the spirit of the invention.

For simplicity, the embodiment shown in FIG. 1 comprises a single outer wall 20 and a single inner wall 35 surrounding the inner reinforcing layer 30. However, it is contemplated that outer wall 20 and inner wall 35 could be constructed in any number of different arrangements. For instance, polymeric tubes of different radii could be placed concentrically within one another, placed around or within a inner reinforcing layer and then melt-processed onto the inner reinforcing layer. Similarly, several lengths of separate tubes could be placed around or within the inner reinforcing layer in an end-to-end fashion and melt-processed onto the inner reinforcing layer. Such techniques may be used to introduce materials having different durometers of hardness or other mechanical characteristics to certain portions of the shaft depending on the desired characteristics. That is, such techniques may be used to construct a catheter shaft having axially and/or radially varying characteristics.

It should also be understood that the embodiment shown in FIG. 1 could further include a series of outer walls or inner walls running along the interior of the inner reinforcing layer without departing from the spirit of the invention. Therefore, the depiction of a single outer wall and a single inner wall in the embodiment shown in FIG. 1 is for simplicity only and is not intended to be limiting.

For instance, U.S. application Ser. Nos. 11/967,219 and 11/967,220 describe a number of different structures and methods of manufacture which could be suitable for construction of the catheter shaft of the present invention. These applications are hereby incorporated by reference as though fully set forth herein.

Figure 2:
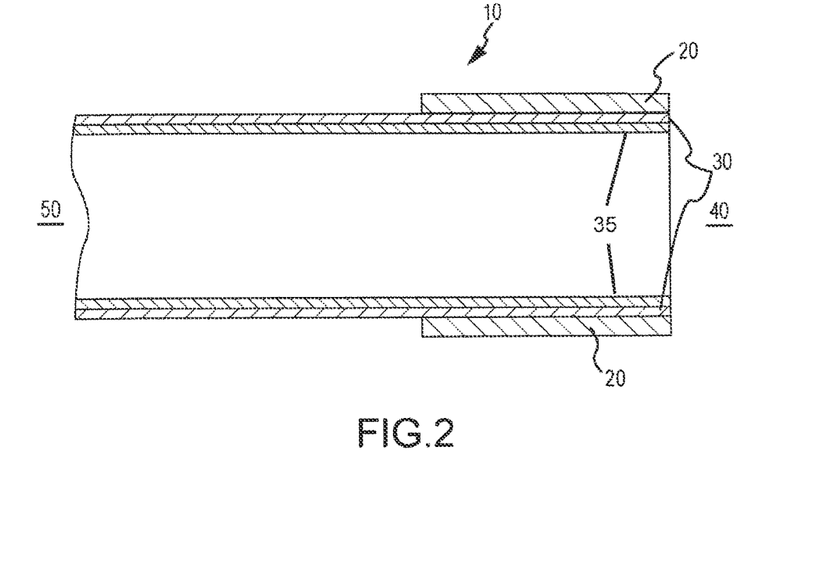
FIG. 2 is a similar longitudinal cross-sectional view of a reinforced catheter shaft which has had the outer layers of material removed from a distal end of the catheter shaft.
Figure 3:
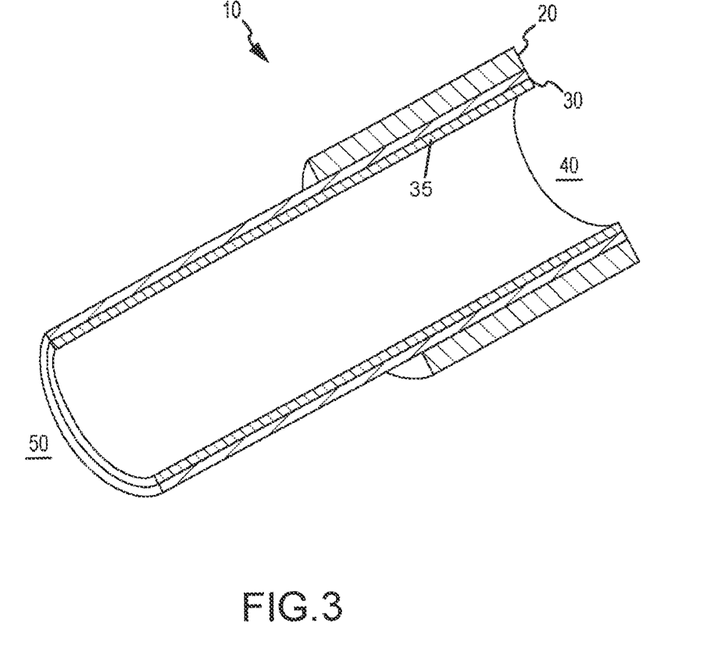
FIG. 3 is an isometric view of the reinforced catheter shaft of FIG. 1 and FIG. 2 which also shows the outer material removed from a distal end of the catheter shaft.

A further step in the basic method of manufacture of the catheter assembly of the invention is illustrated in FIGS. 2-3. In the illustrated embodiment, a portion of the outer layer is removed from the distal end of the catheter shaft 10 while still maintaining the structural integrity of the inner reinforcing layer 30 throughout the entire length of the shaft. The outer layer of material in the distal end of the catheter shaft may be removed using a laser, grinding or other similar methods which create a distal end having a smaller outer diameter than the rest of the shaft. Throughout the remainder of this description, this distal section of the catheter shaft which has had material removed will be referred to as the "exposed portion" of the catheter shaft. However, the use of the term "exposed portion" should not be interpreted to mean that the reinforcing layer 30 is actually exposed. In fact, in particular embodiments of the invention, and though not depicted in FIG. 2, it is preferable that a portion of outer layer 20 remains throughout the axial length of catheter shaft 10, such that reinforcing layer 30 is not exposed or structurally altered in any way.

Figure 2A:
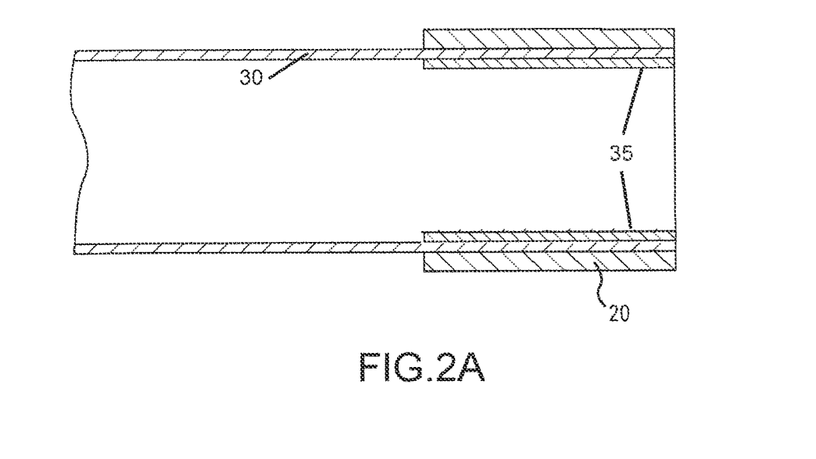
FIG. 2A shows a variation of the embodiment of FIG. 2, in which inner layers of material have also been removed from the distal end of the catheter shaft.

FIG. 2A shows an optional variation of the catheter shaft of FIG. 2, in which a portion of the inner layer 35 and a portion of the outer layer 20 have been removed from the distal end. A portion of the inner layer 35 may be removed, for example, to provide greater flexibility in a portion of the catheter shaft 10. Of course, as with the removal of outer layer 20, it is contemplated that a portion of inner layer 35 may remain throughout the axial length of catheter shaft 10, such that reinforcing layer 30 is not exposed or structurally altered in any way.

Figure 4:
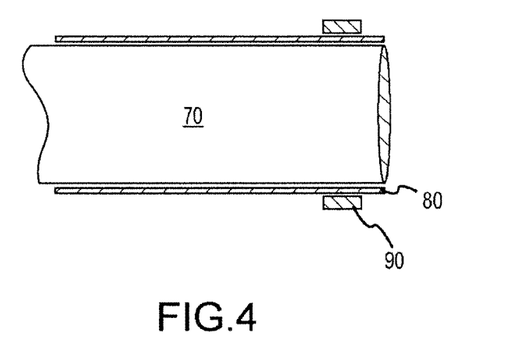
FIG. 4 is a longitudinal cross-sectional view of a separate catheter segment or tip having an outer diameter corresponding closely to the inner diameter of the reinforced catheter shaft. In this particular embodiment, the catheter segment or tip has an inner jacket segment as well as a pull ring.
Figure 8:
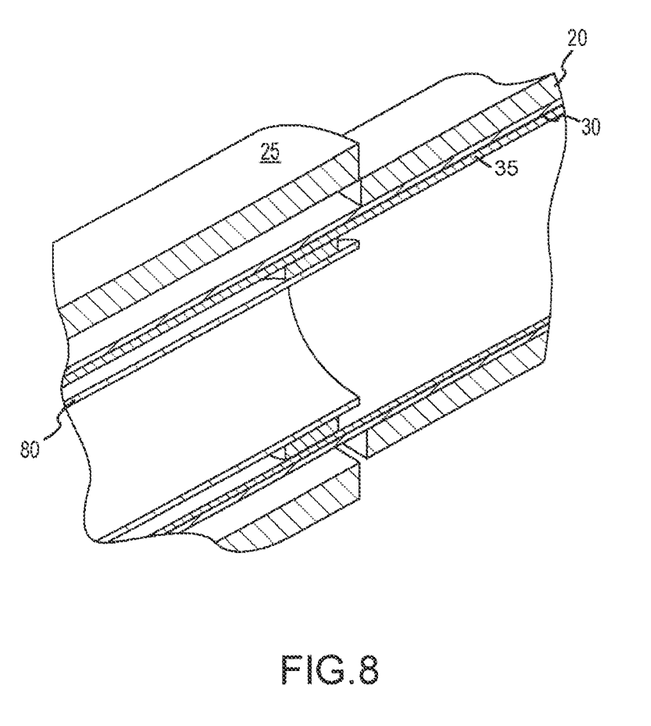
FIG. 8 is an isometric cross-sectional view of FIG. 7.
Figure 9:
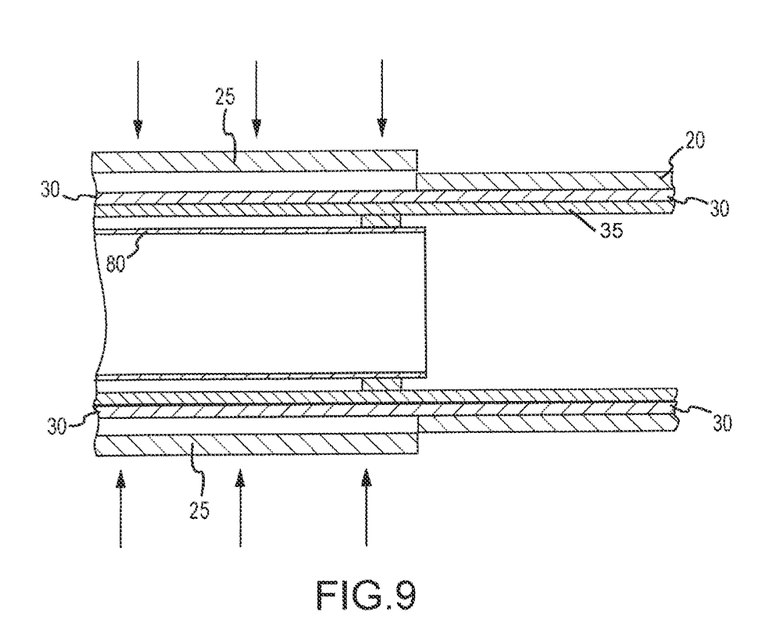
FIG. 9 depicts an embodiment of the present invention which bonds the outer jacket segment of FIGS. 7-8 to the fitted inner jacket segment and catheter shaft members.
Figure 10:
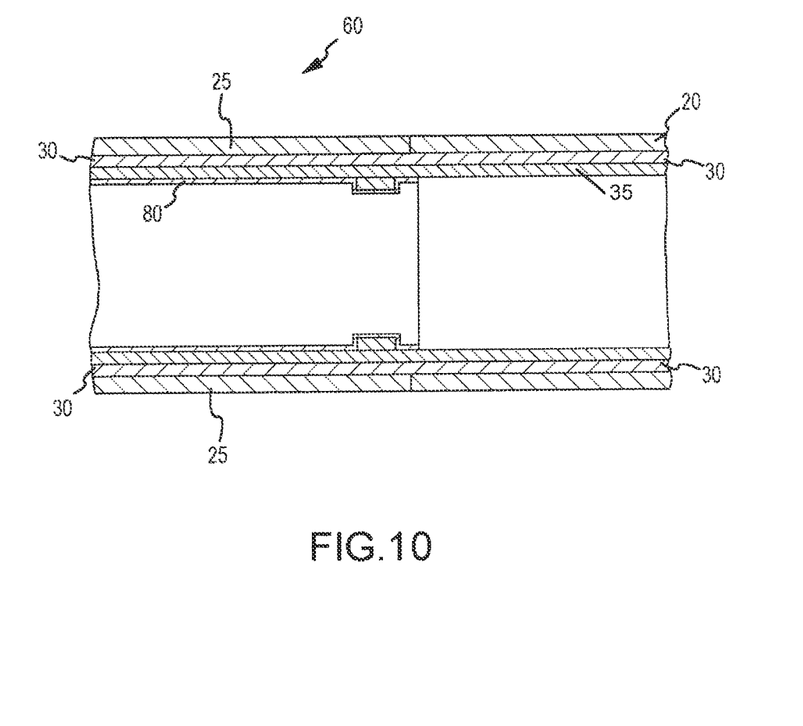
FIG. 10 is a longitudinal cross-sectional view of a bonded embodiment of the present invention showing the reinforced catheter shaft, the separate catheter segment or tip including the inner jacket segment, pull ring and outer jacket segment all joined as a single structure.

FIGS. 4-10 illustrate the assembly of the "catheter segment" or "tip" component 60 of the catheter assembly. As described in more detail below, the catheter segment or tip 60 (as seen in FIG. 10) is formed by reflowing an outer jacket segment 25 onto the exposed distal segment of the catheter shaft 10, and optionally an inner jacket segment 80 at the interior surface of the exposed distal segment of the catheter shaft 10. Building over a mandrel 70, an inner jacket segment 80 is formed about mandrel 70, as shown in FIG. 4. For example, inner jacket segment 80 may be separately extruded and slipped about mandrel 70 or may be formed by wrapping a polymeric tape about mandrel 70. The inner jacket segment 80 may comprise materials of a single durometer or multiple durometers. As with the construction of the catheter shaft described in FIG. 1, the inner jacket segment 80 of the catheter segment or tip 60 need not be limited to a single layer. Catheter segment or tip 60 may also include a pull ring 90 and associated wiring (not shown). As shown in FIG. 4, pull ring 90 is provided around inner jacket segment 80.

Suitable materials for inner jacket segment 80 include, without limitation, polyamides, polyesters, polyurethanes, functionalized polyolefins, polyamide-based thermoplastic elastomers, polyester-based thermoplastic elastomers, styrenic thermoplastic elastomers, functionalized thermoplastic olefins, thermoplastic polyurethanes, ionic thermoplastic elastomers, and any combinations thereof. Specifically suitable materials include, without limitation, Pebax® 6033, Pellethane 2163-60, Pellethane 2163 65D, Fusabond®N MN493D, Fusabond®E MB100D, Fusabond®P M613-05, and Pebax® 6833.

Although the particular embodiment of FIG. 4 shows an inner jacket segment 80 having a length extending distally out of the field of view, it is expressly contemplated that a wide variety of lengths for inner jacket segment 80 would be acceptable for the catheter segment or tip 60 of the completed catheter assembly. For example, the length of the inner jacket segment may be shorter than the length of the inner jacket segment 80 shown in FIG. 4; in one embodiment, for example, the inner jacket segment 80 may be a relatively short length such that inner jacket segment 80 extends axially only slightly beyond either side of the pull ring (for example, about 10% to about 50% of the axial length of the pull ring). The thickness and/or materials of inner jacket segment 80 may be matched or different depending on the desired characteristics.

As described above, a catheter segment or tip, of which inner jacket segment 80 is a part, may be designed for mapping or ablation. It may have a fixed shape designed to accommodate a particular target anatomy or be conformable to any shape it encounters. It may be bi-directional or otherwise steerable and also comprise additional pull rings or wire. Accommodation may also be made for electrodes, sensors or other instruments as well as any conductors or leads necessary to support those elements. Multiple lumens available for irrigation or other purposes are also expressly contemplated. In summary, the spirit of the invention expressly contemplates providing the maximum amount of design flexibility to the catheter segment or tip of the catheter assembly as limited only by the requirements of the application to which the catheter segment or tip is intended.

Figure 5:
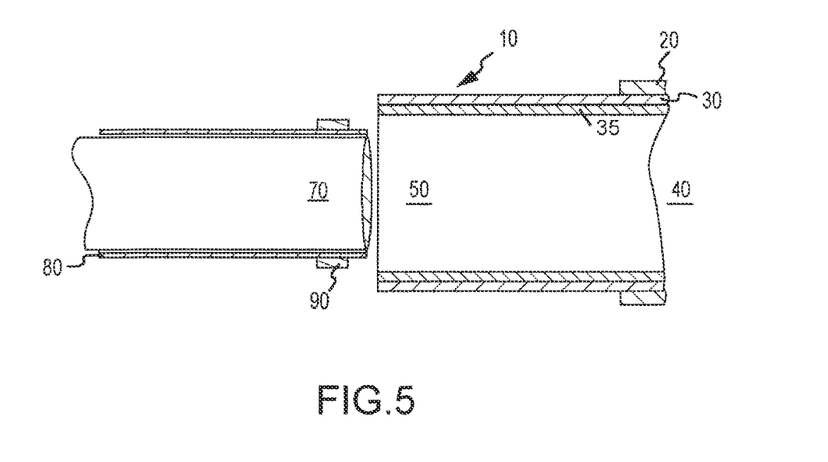
FIGS. 5 and 6 show a longitudinal cross-sectional view of an embodiment of the present invention comprising a reinforced catheter shaft and a separate catheter segment or tip and showing the manner in which the separate catheter segment or tip may be placed within the reinforced catheter shaft.
Figure 6:
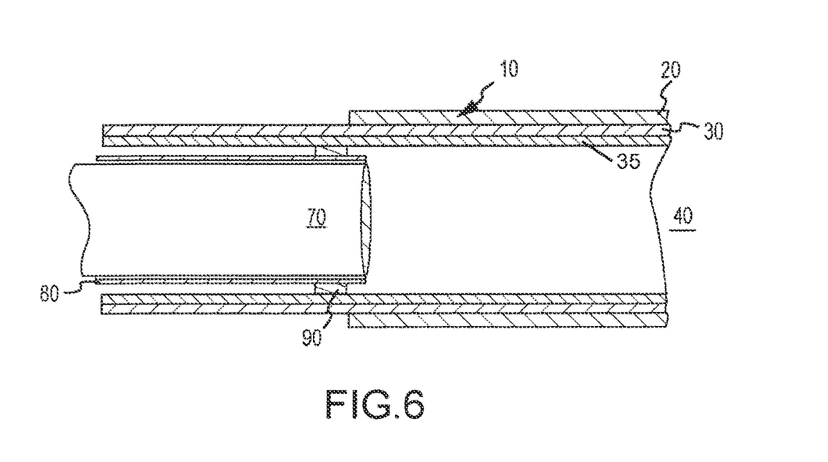

Turning to FIGS. 5-6, further steps of the manufacturing process according to an aspect of the invention are illustrated. The inner jacket segment 80 and the catheter shaft 10 are brought together and the distal end 50 of the catheter shaft 10 is slipped over the inner jacket segment 80 so that the inner reinforcing layer 30 of the catheter shaft 50 closely surrounds the inner jacket segment 80 (as well as pull ring 90 if one is provided).

Figure 7:
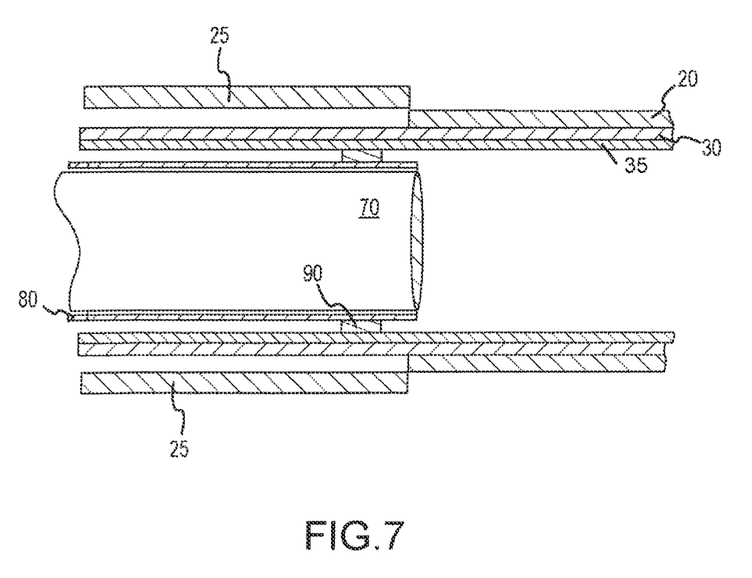
FIG. 7 is a longitudinal cross-sectional view of a reinforced catheter shaft and separate catheter segment or tip as found in FIG. 6 with the addition of an outer jacket segment placed around the entire circumference of the fitted shaft members.

Further steps according to an aspect of the invention at FIGS. 7-8 show the placement of an outer jacket segment 25 which is slipped over the entire exposed catheter shaft/inner jacket segment combination. The outer jacket segment 25 may comprise the same material and be of similar thickness to the outer layer 20 of the catheter shaft 10. However, there is no requirement that it be the same or similar, depending on the physical characteristics desired for the catheter segment or tip. It is generally contemplated however, that the outer jacket segment 25 be chemically compatible with outer layer 20 and inner reinforcing layer 30 in the sense that they can bond effectively to each other. It is within the spirit of the invention for the outer jacket segment 25 to be constructed of segments of different lengths and hardness which can confer different physical properties to different longitudinal sections of the outer jacket. Typically, the outer jacket segment 25 will be formed from a different material having a different durometer hardness from that of the outer layer 20. By removing a portion of the outer layer 20 at the distal end to form the exposed distal segment and replacing that with a different material with a different durometer hardness contained in the outer jacket segment 25, it is possible to customize the curve shape of the distal catheter segment or tip 60 of the catheter shaft 10, advantageously by reflowing only the components in the region of the catheter segment or tip 60 instead of the entire shaft assembly. Similarly, a portion of the inner layer 35 can be removed at the distal end (as seen in FIG. 2A) and be replaced by an inner jacket segment 80 having a different material with a different durometer hardness, so that it is possible to customize the curve shape of the distal catheter segment or tip 60 of the catheter shaft 10.

In some embodiments of the invention, a layer of heat shrink tubing (not shown) is placed over outer jacket segment 25 to impart force as depicted by the arrows in FIG. 9. Heat shrink is preferably a fluoropolymer or polyolefin material such as polytetrafluoroethylene (PTFE) or fluorinated ethylene-propylene copolymer (FEP). As an alternative to heat shrink tubing, the catheter assembly may be placed into a suitable mold prior to subsequent processing. Either heat shrink tubing or a suitable mold may be generally referred to as a "shape retention structure," so named because it retains the overall shape of the catheter assembly (that is, the generally circular axial cross-section) during melt-processing.

As shown in FIG. 9, the catheter assembly may then be melt-processed. Energy (e.g., radiofrequency energy or thermal energy) is applied to the catheter assembly, for example to the outer jacket segment 25 of the catheter assembly, to bond outer jacket segment 25, the exposed portions of outer wall 20 and inner wall 35, inner reinforcing layer 30, and inner jacket segment 80 in a process often referred to as "reflow bonding." Heat shrink tube has a higher melting temperature than outer jacket segment 25, inner reinforcing layer 30, outer wall 20, inner wall 35 and inner jacket segment 80, such that, during the melting process, the heat shrink tube will contract while retaining its tubular shape. The combination of applied energy and pressure exerted by a heat shrink tube forces melted outer jacket segment 25, outer wall 20, inner wall 35 and inner jacket segment 80 to flow and redistribute about the circumference of the catheter assembly and melt together around inner reinforcing layer 30. The reflow process also melts the assembly around pull ring 90. It is appreciated that the reflow process will melt only a local portion of the outer wall 20 and inner wall 35 near the distal end 50, so that the remaining portion of the catheter shaft 10 (including the proximal end 40) will not be heated and will not melt.

Once the catheter assembly has cooled, mandrel 70 can be removed, leaving a central lumen (FIG. 10) extending through the completed catheter assembly. Optionally, heat shrink tubing may also be removed, such that outer layer 20 and outer jacket segment 25 become the outermost layer of the catheter assembly.

FIG. 10 depicts a catheter assembly after the conclusion of the reflow bonding process. That is, FIG. 10 depicts a longitudinal cross section of a catheter assembly formed according to an embodiment of the present invention. One of skill in the art will appreciate that, as a result of the reflow bonding process described above, outer jacket segment 25 as well as any material of outer layer 20 that has not been removed on the exterior side, and inner jacket segment 80 as well as any material of inner layer 35 that is present on the interior side, will completely encapsulate the same continuous inner reinforcing layer 30 that was incorporated into the catheter shaft 10. The reflow bonding of these components forms the distal catheter segment or tip 60 having desired material characteristics that are typically different from the rest of the catheter shaft 10, based on the selection of the materials of the outer jacket segment 25 and the inner jacket segment 80. Advantageously, the inner reinforcing layer 30 is continuous throughout the entire length of the catheter assembly and the interfaces (e.g., bonds) between outer layer 20, outer jacket segment 25, inner layer 35 and inner jacket segment 80 are substantially seamless without any dead spaces or material voids. This reduces the likelihood of material cracking and other failures of catheter assembly. FIG. 10 shows discrete regions of the inner jacket segment 80 and the inner layer 30 in the catheter segment 60 after the reflow process merely for schematic illustration. In reality, there will not be a clear delineation of the materials after they melt and solidify to form a combined inner layer of the catheter segment 60. Similarly, if the outer layer 20 is not completely removed and a portion of the outer layer 20 remains in the catheter segment 60, it will be combined with the outer jacket segment 25 during the reflow process to form a combined outer layer of the catheter segment 60.

One of skill in the art will recognize that the method of manufacture of the present invention improves upon previous methods by facilitating attachment of a large variety of catheter segments and tips to a catheter shaft in a manner that still yields a structurally continuous catheter assembly. Thus, one set of manufacturing processes and equipment could be used to create the relatively long catheter shafts that are required to deliver therapeutic instruments through the vasculature to the heart. Then, relatively smaller and more specialized manufacturing processes and equipment could be used to create the virtually limitless variety of catheter segments and tips that various procedures require. By reflowing only the catheter segment or tip over the exposed inner reinforcing layer of the catheter shaft, a structurally continuous catheter assembly can be assembled in modules relatively quickly and inexpensively.

In some embodiments of the invention, it may be desirable for the catheter assembly to be radiopaque. Thus, it is contemplated that one or more outer layer 20, outer jacket segment 25, inner jacket segment 80 or inner layer 35 may include a radiopaque filler. Suitable radiopaque fillers include, without limitation, barium sulfate, bismuth subcarbonate, bismuth trioxides, bismuth oxychloride, tungsten, tantalum, platinum, gold, and any combinations thereof. Radiopaque nanoclays may also be employed. As an alternative to the use of radiopaque fillers, or in addition to the use of radiopaque fillers, a radiopaque marker (not shown) may be included in the catheter assembly.

Although several embodiments of this invention have been described above with a certain degree of particularity, those skilled in the art could make numerous alterations to the disclosed embodiments without departing from the spirit or scope of this invention. For example, a catheter formed according to the present invention may have varying sizes and varying uses, including, but not limited to, the treatment of atrial fibrillation and the treatment of atrial tachycardia.

Although a number of polymers have been mentioned in this application any number of polymers have been suggested for use in medical device and catheter applications, including: polyethylene; polyetherimide; polypropylene; polyetheretherketone (PEEK); polytetrafluoroethylene (PTFE) or Teflon (DuPont, Wilmington, Del.); Ultra High Molecular Weight (UHMW) polyethylene; high density polyethylene (HDPE); polyimide; polyaryletherketones; polyetheretherketones; polyurethane; polypropylene; oriented polypropylene; polyethylene; crystallized polyethylene terephthalate; polyethylene terephthalate; polyester; polyoxymethylene or Delrin (DuPont, Wilmington, Del.); polyamide-imide (PAI) or TORLON (Solvay Advance Polymers, Alpharetta, Ga.); polyoxymethylene (POM), acetal resin, or Delrin (DuPont, Wilmington, Del.); and polyvinylidene fluoride or Kynar (Atochem Corporation). One of skill in the art is familiar with selecting the appropriate polymer or polymer combinations to achieve the flexibility and lubricity properties desired. In some examples, flexible elostomers, such as polyether block amide—PEBA, such as Pebax®, a registered trademark of Atofina Chemicals, are a preferred polymer for use in the invention and methods especially for the external coating of the catheters, and especially in varying hardness according to the Durometer D or Shore D scale, known in the art.

One of ordinary skill in the art will also appreciate that other modifications could be made to the catheter assembly herein without departing from the spirit and scope of the present invention. For example, the catheter assembly could be made steerable, as described in U.S. application Ser. No. 11/647,313, filed 29 Dec. 2006 ("the '313 application"), or with embedded internal components, for example as described in U.S. application Ser. No. 11/646,578, filed 28 Dec. 2006 ("the '578 application"). Both the '313 application and the '578 application are hereby incorporated by reference as though fully set forth herein.

In addition, it is contemplated that a catheter according to the present invention may be manufactured using alternative techniques.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of manufacturing a catheter assembly, comprising the steps of:
   providing a catheter shaft having a proximal end, a distal end, an outer layer, and an inner reinforcing layer;
   removing at least a portion of said outer layer from a length of the distal end of the catheter shaft in order to expose a distal segment of the catheter shaft having an exposed exterior region;
   providing an inner jacket segment having a proximal end and a distal end;
   axially engaging the inner jacket segment with an interior surface of the distal segment of the catheter shaft;
   providing an outer jacket segment around at least the exposed exterior region of the distal segment of the catheter shaft; and
   bonding the distal segment of the catheter shaft to the inner jacket segment and the outer jacket segment.

2. The method of claim 1, wherein the outer jacket segment and the outer layer comprise different materials with different durometer hardness values.

3. The method of claim 1, wherein the catheter shaft further comprises an inner layer.

4. The method of claim 3, further comprising the additional step of removing at least a portion of said inner layer from a distal end of the catheter shaft to form an exposed interior region of the distal segment of the catheter shaft, wherein the exposed interior region is disposed around the inner jacket segment.

5. The method of claim 1, wherein the length of the exposed distal segment of the catheter shaft is at least as long as the length of the inner jacket segment.

6. The method of claim 1, wherein the outer layer of the catheter shaft comprises a melt processable polymer.

7. The method of claim 1, wherein the removing step comprises grinding.

8. The method of claim 1, wherein the removing step comprises removal with a laser.

9. The method of claim 1, wherein the inner jacket segment comprises a melt processable polymer.

10. The method of claim 1, wherein the outer jacket segment has varying hardness along its length.

11. The method of claim 1, wherein the inner jacket segment further comprises a pull ring operatively connected thereto.

12. The method of claim 1, further comprising applying energy to the outer jacket segment, the exposed distal segment of the catheter shaft, and the inner jacket segment to form a substantially unitary catheter shaft.

13. The method of claim 12, further comprising forming a heat-shrink tube about the outer jacket segment prior to the energy applying step.

14. The method of claim 12, further comprising applying energy to the outer jacket segment, the exposed distal segment of the catheter shaft, and the inner jacket segment in a manner that does not heat the proximal end of the catheter shaft.

15. A method of forming a catheter assembly, comprising the steps of:
   providing a catheter shaft having an outer layer of a first material and an inner reinforcing layer;
   removing at least a portion of said outer layer from a length of the catheter shaft in order to expose a distal segment of the catheter shaft;
   providing an inner jacket segment having a proximal end and a distal end;
   axially engaging the exposed distal segment of the catheter shaft with the proximal end of the inner jacket segment, providing an outer jacket segment of a second material around the exposed distal segment of the catheter shaft; and bonding the catheter shaft to the outer jacket segment and the inner jacket segment.

16. The method according to claim 15, wherein the inner reinforcing layer of the catheter shaft extends continuously over the entire length of the catheter shaft and the inner jacket and outer jacket segments.

17. The method according to claim 15, further comprising applying energy to the outer jacket segment, the inner reinforcing layer of the catheter shaft, and the inner jacket segment in a manner that does not heat a portion of the outer layer of the catheter shaft which is disposed away from the distal end of the catheter shaft.

18. The method according to claim 15, wherein the first material and the second material are selected from the group consisting of polyamides, polyurethanes, polyesters, functionalized polyolefins, polycarbonates, and any combinations thereof.

19. The method according to claim 15, wherein the first material and the second material are selected from the group consisting of polyamide-based thermoelastic elastomers, polyester-based thermoplastic elastomers, thermoplastic polyurethanes, styrenic thermoplastic elastomers, and any combinations thereof.

20. A catheter assembly formed according to a method comprising the steps of:
providing a catheter shaft having a proximal end, a distal end, an outer layer and an inner reinforcing layer;
removing at least a portion of said outer layer from a length of the distal end of the catheter shaft in order to expose a segment of the catheter shaft;
providing an inner jacket segment having a proximal end and a distal end;
axially engaging the exposed segment at the distal end of the catheter shaft with the inner jacket segment such that the inner jacket segment is positioned within and adjacent the exposed segment of the catheter shaft; and
forming an outer jacket segment around the exposed catheter shaft segment to operatively connect the catheter shaft to the inner jacket segment.

21. The catheter assembly according to claim 20, wherein the outer jacket segment has varying hardness along it length.

22. The catheter assembly according to claim 20, wherein the outer jacket segment has a lower durometer than the catheter shaft.

23. The catheter assembly according to claim 20, wherein the inner jacket segment further comprises a pull ring attached to an inner layer of the inner jacket segment.

24. The catheter assembly according to claim 23, wherein the pull ring is operatively connected to a plurality of pull wires which extend through the inner jacket segment and catheter shaft to a proximal end of the catheter shaft.

25. A method of manufacturing a catheter assembly, comprising:
providing a catheter shaft having a proximal end, a distal end, an outer layer of a first material, and an inner reinforcing layer;
removing at least a portion of the outer layer from a length of the distal end of the catheter shaft in order to expose a distal segment of the catheter shaft having an exposed exterior region;
providing an outer jacket segment of a second material around at least the exposed exterior region of the distal segment of the catheter shaft, the second material being different from the first material; and
bonding the outer jacket segment to the exposed exterior region of the distal segment of the catheter shaft.

26. The method of claim 25, wherein bonding the outer jacket segment to the exposed exterior region of the distal segment of the catheter shaft comprises applying energy to the outer jacket segment and the distal segment of the catheter shaft.

27. The method of claim 26, wherein the energy is applied in a manner that does not heat the proximal end of the catheter shaft.

28. The method of claim 25, further comprising:
providing an inner jacket segment at an interior surface of the distal segment of the catheter shaft; and
bonding the inner jacket segment to the interior surface of the distal segment of the catheter shaft.

29. The method of claim 28, wherein bonding the outer jacket segment to the exposed exterior region of the distal segment of the catheter shaft and bonding the inner jacket segment to the interior surface of the distal segment of the catheter shaft comprise applying energy to the outer jacket segment, the inner jacket segment, and the distal segment of the catheter shaft.

* * * * *